United States Patent [19]

Boatright

[11] 4,061,740
[45] Dec. 6, 1977

[54] LIQUID COMPOSITIONS CONTAINING A POLYETHYLENE GLYCOL SAFENER AND AN ORGANOPHOSPHORUS PESTICIDE

[75] Inventor: Alfonso Boatright, Burlington, N.J.

[73] Assignee: American Cyanamid Company, Stamford, Conn.

[21] Appl. No.: 733,648

[22] Filed: Oct. 18, 1976

Related U.S. Application Data

[63] Continuation-in-part of Ser. No. 632,942, Nov. 18, 1975, abandoned.

[51] Int. Cl.$^2$ ............................................. A01N 9/36
[52] U.S. Cl. .................................................. 424/202
[58] Field of Search .................... 424/202; 260/327 M

[56] References Cited

U.S. PATENT DOCUMENTS

| 3,449,493 | 6/1969 | Addor | 424/202 |
| 3,470,207 | 9/1969 | Addor | 424/202 |
| 3,898,305 | 8/1975 | Beriger et al. | 260/327 M |

OTHER PUBLICATIONS

Chemical Abstracts, vol. 66 (1967), p. 54567w.

*Primary Examiner*—V. D. Turner
*Attorney, Agent, or Firm*—Harry H. Kline

[57] ABSTRACT

There are provided novel compositions comprising polyethylene glycol solvents of average molecular weights of 200 to 600 and an organophosphorous pesticide, wherein said compositions are effective for the control of root-knot nematodes (*Meloidogyne incognita*) while characterized by markedly low mammalian dermal toxicity.

8 Claims, No Drawings

LIQUID COMPOSITIONS CONTAINING A POLYETHYLENE GLYCOL SAFENER AND AN ORGANOPHOSPHORUS PESTICIDE

This application is a continuation-in-part of my co-pending application, Ser. No. 632,942, filed Nov. 18, 1975, now abandoned.

Agricultural pesticides employed for the control of pests damaging and destroying food and fodder crops are by their very nature more or less toxic to mammals. Thus, they represent a distinct hazard to the individuals engaged in the application and use thereof. Although such pesticides may enter the human body via ingestion and/or inhalation, the most commonly encountered mode of entry is by absorption through the skin. Consequently, it is of prime interest to those who manufacture pesticidal agents or formulate them to find compositions of such pesticides which, while fully retaining their effectiveness for the control of said agricultural pests, will have a decreased mannalian dermal toxicity.

It is known that 2-diethoxyphosphinylimino-1,3-dithietane or dithiole represented by formula:

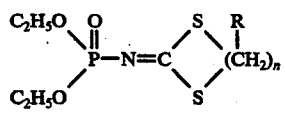

where R is hydrogen or methyl and n is 1 or 2 is effective for the control of root-knot nematodes (*Meloidogyne incognita*). As a nematocide, 2-diethoxyphosphinylimino-1,3-dithietane or 2-diethoxyphosphinylimino-1,3-dithiolane, for instance, may be applied to the soil either as a solid (powdered or granular) formulation or as a dilute aqueous spray prepared from soluble solid or liquid concentrates. Solid formulations containing the latter dithietane or dithiolane consist of a powdered or granular carrier, such as an attapulgite type of a clay, diatomaceous earth, and the like, containing from 1 to 50%, by weight, and preferably from 5 to 15%, by weight, of 2-diethoxyphosphinylimino-1,3-dithietane. In addition, said formulations may also contain, if desired, 1 to 5%, by weight, of any commercially available surfactant.

It should be noted, that as a general rule, organophosphorus pesticides have limited storage stability when formulated in combination with the above-named clays. However, if diethylene glycol, triethylene glycol or a polyethylene glycol is incorporated into the above referred-to formulations in amounts ranging from about 1 to 20%, by weight, of the overall formulation, then the decomposition of said organophosphorus pesticides is significantly retarded.

Liquid formulations of the hereinabove defined 2-diethoxyphosphinylimino-1,3-dithietane or dithiolane are usually prepared by dissolving 5 to 70%, by weight, of active ingredient in a solvent such as benzene, toluene, xylene, aromatic petroleum distillates, $C_1$-$C_3$ alcohols, ketones such as acetone, methyl ethyl ketone, methyl butyl- and isobutyl ketone, cyclohexanone and the like, or mixtures thereof. In addition, said solution may also contain 1 to 10%, by weight, of a surfactant.

Solid and liquid formulations of 2-diethoxyphosphinylimino1,3-diethietane or dithiolane prepared by the above methods are eminently suitable for the control of root-knot nematodes (*Meloidogyne incognita*) and other insect and acarid pests. All of these formulations are, however, highly toxic to mammals and are rapidly absorbed through the skin.

Surprisingly, it has been found that if, in the above-noted, liquid formulations polyethylene glycols of average molecular weights of 200 to 600 are substituted for the aforementioned solvents, the pesticidal activity of 2-diethoxyphosphinylimino-1,3-diethietane or dithiolane is retained. However, the mammalian dermal toxicity is unexpectedly reduced significantly by a factor of 10 to 15.

Thus, the novel liquid compositions of the present invention comprises a polyethylene glycol solvent having an average molecular weight of 200 to 600 and containing from 5% to 70%, by weight, of 2-diethoxyphosphinylimino-1,3-dithietane or dithiolane and if desired, from 1% to 10%, by weight, of a surfactant. These formulations are distinguished by their excellent activity and by their markedly reduced mammalian dermal toxicity.

The present invention is further illustrated by the non-limiting examples set forth below.

EXAMPLE 1 to 35

General Procedure for the Preparation of Liquid Formulations Containing (a) 2-Diethoxyphosphinylimino-1,3-diethietane, or (b) 2-Diethoxyphosphinylimino-1,3-dithiolane or (c) 2-Diethoxyphosphinyl-4-methyl-1,3-dithiolane In a suitable vessel X%, by weight, of real above-named dithietane or dithiolane, Y%, by weight, of an emulsifier, or mixture of emulsifiers and Z%, by weight, of solvent are mixed and stirred to a homogeneous solution. If needed, the solution may be clarified by filtration or decantation.

In these formulations the values of X and Y are predetermined by choice, however since the 2-diethoxyphosphinylimino-1,3-dithietane samples are of technical grade less than 100% pure, the actural amount of technical grade material needed is determined by the formula:

$$X' = \frac{X}{\% \text{ purity of sample}} \times 100$$

wherein X' represents the %, by weight, of technical sample needed in the above solution. The sum of X', Y and Z is equal to 100%. Alternatively, if it is desired to omit the emulsifier from the formulation, then X' + Z = 100%.

Solutions made with the polyethylene glycols of the present invention are prepared in similar fashion. However, since some of the solvents are highly viscous, they are first prewarmed to a flowable liquid to which the other components are then added and the whole stirred to a homogeneous solution.

The percent, by weight, composition of these formulations is summed up in Table (I), [Examples 1–14]; Table (II), [Examples 15–25]; and Table (III), [Examples 26–34].

Additionally, the $LD_{50}$ mg/kg body weight data as obtained in Example 36, are also included in the Tabels below for comparative purposes.

Table I

Compositions by Weight % of the Liquid Formulations Obtained in Examples 1 to 14 utilizing 2-Diethoxyphosphinylimino-1,3-dithietane Including Dermal $LD_{50}$ Data Obtained in Example 36

Composition of Formulations by Weight Percent

| Ex. | Solvent | Active Ingredient as is | Active Ingredient real | Other Components | $LD_{50}$; mg/kg |
|---|---|---|---|---|---|
| 1 | Xylene; 64.96 | 28.64 | 24.80 | Blend of nonionic and anionic surfactants; 6.4 | 23.0 |
| 2 | Xylene; 20.2 | 79.8 | 66.2 | — | No more than 29.4 |
| 3 | Cyclohexanone; 20.2 | 79.8 | 66.2 | — | Less than 22.5 |
| 4 | Aromatic naphtha; 20.2 | 79.8 | 66.2 | — | Less than 30 |
| 5 | N-methyl-pyrrolidone; 20.2 | 79.8 | 66.2 | — | Less than 22.5 |
| 6 | Xylene; 14.6 | 73.9 | 61.33 | Polyoxyethylene ether Polyoxyethylene glycerides alkyl aryl ether-alkyl aryl sulfonate blend 8.5; Polyisobutylene 3.0; | Less than 29.5 |
| 7 | Propylene glycol; 72.2 | 27.8 | 23.02 | — | 76.4 |
| 8 | Tetraethylene glycol; 70 | 30.0 | 24.84 | — | 106.4 |
| 9 | Polyethylene glycol "200"; 75 | 25.0 | 22.75 | — | 143.1 |
| 10 | Polyethylene glycol; "300"; 75 | 25.0 | 22.75 | — | 261.3 |
| 11 | Polyethylene glycol "400"; 77 | 23.0 | 20.93 | — | 325.0 |
| 12 | Polyethylene glycol "400"; 70.88 | 29.12 | 26.50 | — | 325.0 |
| 13 | Polyethylene glycol "400"; 76.15 | 23.85 | 21.7 | — | 377.0 |
| 14 | Polyethylene glycol "600"; 75 | 25 | 22.5 | — | 233.0 |

Table II

Compositions by Weight % of the Liquid Formulation Obtained in Example 15 to Example 25 utilizing 2-Diethoxyphosphinylimino-4-methyl-1,3-dithiolane Including Dermal $LD_{50}$ Data Obtained in Example 36

Composition of Formulations by Weight Percent

| Ex. | Solvent | Active Ingredient As is | Active Ingredient Real | Other Components | $LD_{50}$; mg/kg |
|---|---|---|---|---|---|
| 15 | Polyethylene glycol "200"; 74.2 | 25.8 | 22.9 | — | 108 |
| 16 | Polyethylene glycol "400"; 74.4 | 25.6 | 22.7 | — | 199 |
| 17 | Polyethylene glycol "600"; 74.2 | 25.8 | 22.9 | — | 195 |
| 18 | Polyethylene glycol "200"; 49.7 | 50.3 | 44.7 | — | 51 |
| 19 | Polyethylene glycol "400"; 49.7 | 50.3 | 44.7 | — | 51 |
| 20 | Polyethylene glycol "600"; 49.2 | 50.8 | 45.1 | — | 57 |
| 21 | Polyethylene glycol "200"; 27.1 | 72.9 | 64.7 | — | 39 |
| 22 | Polyethylene glycol "400"; 26.8 | 73.2 | 65.0 | — | 51 |
| 23 | Polyethylene glycol "600"; 26.6 | 73.4 | 65.2 | — | 43 |
| 24 | **Xylene q.s. ad. 100 | 26.5 | | Non-ionic polymeric emulsifier; 10.0 | 27 |
| 25 | **Xylene q.s. ad. 100 | | 47.7 | High boiling aromatic solvent; 12; nonionic - 7.0; and anionic - 1.0; emulsifiers | 16.8 |

** = Included for comparison, typical formulation

Table III

Compositions by Weight % of the Liquid Formulations Obtained in Examples 26 to 34 Utilizing 2-Diethoxyphosphinylimino-1,3-dithiolane Including Dermal $LD_{50}$ Data Obtained in Example 35

Composition of Formulations by Weight Percent

| Ex. | Solvent | Active Ingredient As is | Active Ingredient Real | Other Components | $LD_{50}$ |
|---|---|---|---|---|---|
| 26 | Polyethylene glycol "200"; 71.0 | 29.0 | 22.65 | — | |
| 27 | Polyethylene glycol "400"; 71.2 | 28.8 | 22.49 | — | 131 |
| 28 | Polyethylene glycol "600"; 71.0 | 29.0 | 22.65 | — | 99 |
| 29 | Polyethylene glycol "200"; 44.2 | 55.8 | 43.58 | — | 26 |

Table III-continued
Compositions by Weight % of the Liquid Formulations Obtained in Examples 26 to 34 Utilizing 2-Diethoxyphosphinylimino-1,3-dithiolane Including Dermal $LD_{50}$ Data Obtained in Example 35

| | | Composition of Formulations by Weight Percent | | | |
| | | Active Ingredient | | | |
| Ex. | Solvent | As is | Real | Other Components | $LD_{50}$ |
|---|---|---|---|---|---|
| 30 | Polyethylene glycol "400"; 44.0 | 56.0 | 43.74 | — | 31 |
| 31 | Polyethylene glycol "600"; 44.0 | 56.0 | 43.74 | — | |
| 32 | Polyethylene glycol "200"; 19.1 | 80.9 | 63.18 | — | |
| 33 | Polyethylene glycol "400"; 19.4 | 80.6 | 62.95 | — | |
| 34 | Polyethylene glycol "600"; 18.9 | 81.1 | 63.34 | — | |
| 35 | Cyclohexanone; 32.0 | 30.75 | 24.55 | Aromatic hydrocarbon solvent; 29.1; nonionic emulsifier; 8.0 | 21 |

EXAMPLE 36

General Method for the Evaluation of Dermal Toxicity of the Liquid Formulations Prepared in Examples 1 to 14 using Male Albino Rabbits as the Test Animal

Materials a: Five male albino rabbits weighing approximately 2.2 to 3.5 kilograms are selected for each dosage level. The hair is shaved from the entire trunk.

b: Saran tubing or "Vinylite" film, VU 1900, 12 inches wide, 0.04 millimeters in thickness and long enough to fit around the rabbit.

c: One felt cloth bandage measuring approximately 9×18 inches.

d: Four pieces of 1½ inches adhesive tape approximately 14 inches long.

Procedure a: The animal is placed on the plastic film and then is wrapped and the film secured to the animal's body with adhesive tape.

b: The test material is injected under the plastic at the selected dosage level with an appropriate size needle and syringe.

c: The felt cloth is then placed under the belly and brought up around the animal and secured with the two remaining strips of adhesive tape.

Evaluation

Twenty-four hours after dosing the "cuff" is removed and any remaining material is brushed away. If the test material cannot be removed, the animal is fitted with a fiber collar which prevents the animal from licking the treatment area. The animals are observed for 14 days, post dosing, noting signs of toxicity, skin irritation and mortality. At the end of 14 days, the animals are sacrificed and weighed.

From the data thus obtained, the dermal $LD_{50}$ values (mg/kg body weight) are calculated for the formulations obtained in Examples 1 to 35. The $LD_{50}$ data are included in Table (I), (II) and (III) above, and are also graphically illustrated hereinbelow in Table (IV) for Examples 1–14, where it can be clearly seen that liquid formulations containing the polyethylene glycols of the present invention have markedly decreased the dermal toxicity of 2-diethoxyphosphinylimino-1,3-dithietane.

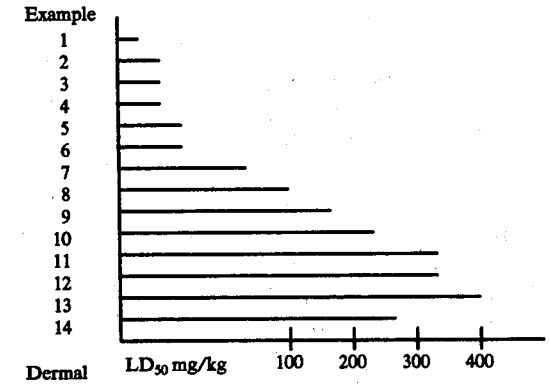

Table IV
Dermal Toxicity of Liquid Formulations Containing 2-Diethoxyphosphinylimino-1,3-diethane, Using Male Albino Rabbits as the Test Animal, Ratings are Given as Dermal $LD_{50}$, mg/kg, Values.

EXAMPLE 37

Evaluation of a liquid formulation consisting of a solution of 2-diethoxyphosphinylimino-1,3-dithietane in polyethylene glycol for the control of root-knot nematode (Meloidogyne incognita) on tomato in the greenhouse.

Materials

A. Formulations
1. 2-Diethoxyphosphinylimino-1,3-dithietane, 91% real. (Active ingredient; a.i.)
2. Liquid formulation consisting of 20.9%, by weight, of a.i. and 79.1%, by weight, of polyethylene glycol of an average molecular weight of 400.
3. Polyethylene glycol blank.

B. Plant
Tomato (Lycopersicon esculentum; Cv. Bonny Best).

C. Infective Agent
Root-knot Nematode (Meloidogyne incognita) inoculum.

Application Rates/liter of potting soil
(equivalent to pound/acre - broadcast)

2-Diethoxyphosphinylimino-1,3-dithietane at 0.75 mg, 1.5 mg and 3.0 mg/liter of soil. Polyethylene glycol blank at 14.4 mg/liter of soil.

Procedure

All compounds are made up as acetone solutions. One liter of moist potting soil is placed in a suitable stainless steel beaker. One ml of candidate solution is distributed, drop by drop, over the surface of the soil. The beaker is then capped and placed on an off-center rotary mixer and mixed for 2 minutes (about 60 revolutions). After mixing, the soil is divided between two 0.5 liter paper cups by filling the cups half full of soil, then distributing 25 ml root-knot nematode inoculum on the soil and filling the remainder of the container with treated soil. Seedling tomato plants are transplanted into the cups of soil the same day, watered and removed to the greenhouse. After about 4 weeks, the tomato plants are carefully removed from the containers, the soil washed from the roots, and the roots are then examined for nematode galling.

The roots are indexed for galling by the following system:

O = No visible galling
T = Less than 1% of roots with galls.
1 = 1–5% of roots galled
2 = 6–10% of roots galled
3 = 11–20% of roots galled
4 = 21–30% of roots galled
5 = 31–40% of roots galled
6 = 41–50% of roots galled
7 = 51–60% of roots galled
8 = 61–70% of roots galled
9 = 71–80% of roots galled
10 = 81–100% of roots galled The results obtained are summarized in Table V below:

Evaluation of a Liquid Formulation of 2-Diethoxy-phosphinylimino-1,3-dithietane in Polyethylene Glycol for the Control of Root-knot Nematode (*Meloidogyne incognita*) on Tomato in the Greenhouse

| Formulation | Rate mg/l Active Ingredient | Root-knot index 1 | 2 | 3 | Average of 3 Replicates |
|---|---|---|---|---|---|
| 1 | 0.75 | 8 | 8 | 5 | 7.0 |
|   | 1.5 | 6 | 6 | 2 | 4.7 |
|   | 3.0 | 0 | 0 | T | 0-T |
| 2 | 0.75 | 9 | 8 | 8 | 8.3 |
|   | 1.5 | 1 | 1 | 1 | 1.0 |
|   | 3.0 | 0 | 0 | 0 | 0.0 |
| 3 | 14.4 | 10 | 10 | 10 | 10.0 |
| Infected Control | — | 10 | 10 | 10 | 10.0 |
| Non-infected Control | — | 0 | 0 | 0 | 0.0 |

Thus, it can be seen from the above data that with 2-diethoxyphosphinylimino-1,3-dithietane alone (Formulation 1) protection of the tomato roots from the root-knot nematode is poor at both 0.75 mg/l and 1.5 mg/l of soil and excellent at 3.0 mg/l of soil; while the solution of this compound in polyethylene glycol (Formulation 2) provides inadequate protection at 0.75 mg/l of soil and excellent protection both at 1.5 mg/l and 3.0 mg/l of soil.

I claim:

1. A composition comprising in combination from 95 to 30%, by weight, of a polyethylene glycol solvent of an average molecular weight of 200 to 600 and from 5 to 70%, by weight, of an agent of the formula:

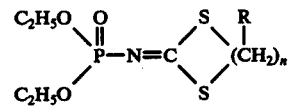

where R is hydrogen or methyl and *n* is an integer from 1 to 2, distinguished by excellent nematocidal and insecticidal activity combined with markedly decreased mammalian dermal toxicity.

2. The composition according to claim 1 wherein said polyethylene glycol is of an average molecular weight of 400.

3. The composition according to claim 1 comprising 75%, by weight, to 85%, by weight, of a polyethylene glycol of an average molecular weight of 400 and from 25%, by weight, to 15%, by weight, of the pesticidal solute of claim 1.

4. The composition according to claim 1 wherein said composition contains 2 pounds per gallon of said agent and said polyethylene glycol solvent is of an average molecular weight of 400.

5. The composition according to claim 1 wherein the agent is: 2-diethoxyphosphinylimino-1,3-dithietane.

6. The composition according to claim 1 wherein the agent is: 2-diethoxyphosphinylimino-4-methyl-1,3-dithiolane.

7. The composition according to claim 1 wherein the agent is: 2-diethoxyphosphinylimino-1,3-dithiolane.

8. A method for the control of nematodes which comprises applying to nematode infected soil an effective amount of the composition of claim 1 ranging from 1.5 mg/l to 3.0 mg/l of soil.

* * * * *

UNITED STATES PATENT OFFICE
CERTIFICATE OF CORRECTION

PATENT NO. : 4,061,740
DATED : December 6, 1977
INVENTOR(S) : Alfonso Boatright

It is certified that error appears in the above-identified patent and that said Letters Patent are hereby corrected as shown below:

Column 1, line 23, "dithiole" should read as --dithiolane--.
Column 1, lines 24 to 29, the formula:

should read as:

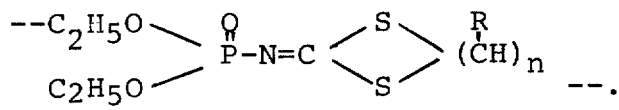

Column 8, Lines 26 through 30, the formula:

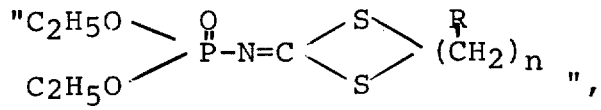

should read as:

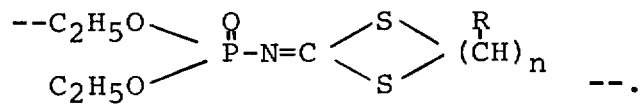

Signed and Sealed this

Twenty-fifth Day of April 1978

[SEAL]

Attest:

RUTH C. MASON
Attesting Officer

LUTRELLE F. PARKER
Acting Commissioner of Patents and Trademarks